Figure 1:
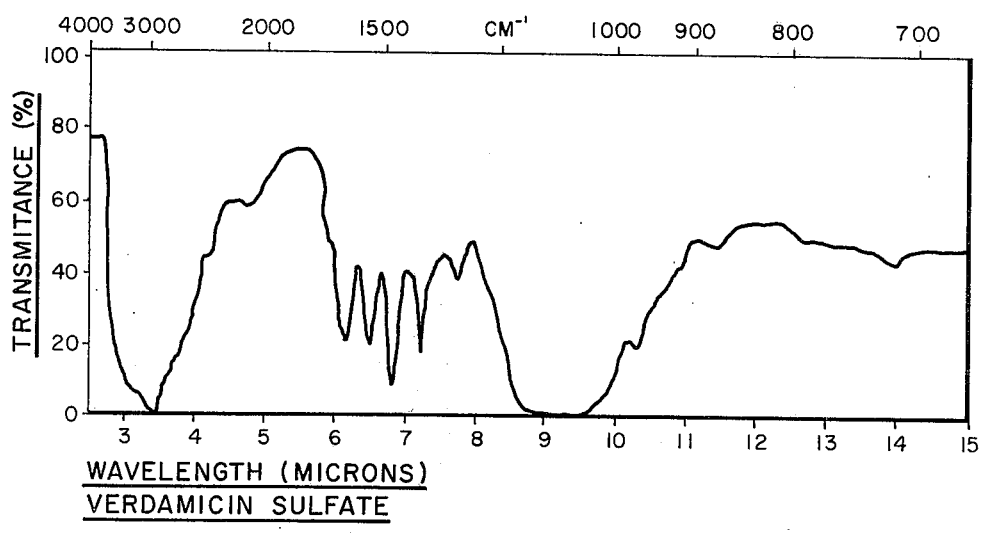

United States Patent [19]

Weinstein et al.

[11] 3,988,316

[45] Oct. 26, 1976

[54] ANTIBIOTICS SISOMICIN AND VERDAMICIN I AND COMPLEX CONTAINING SAME

[75] Inventors: Marvin J. Weinstein; Gerald H. Wagman, both of East Brunswick; Joseph A. Marquez, Montclair, all of N.J.

[73] Assignee: Schering Corporation, Kenilworth, N.J.

[22] Filed: Feb. 18, 1975

[21] Appl. No.: 550,395

Related U.S. Application Data

[63] Continuation-in-part of Ser. No. 426,163, Dec. 19, 1973, abandoned, which is a continuation-in-part of Ser. No. 208,907, Dec. 16, 1971, abandoned, which is a continuation-in-part of Ser. No. 58,050, July 24, 1970, abandoned.

[52] U.S. Cl. .................................. 536/17; 424/180; 424/181; 195/80 R
[51] Int. Cl.² .................. A61K 31/71; C07H 15/22

[58] Field of Search ............................ 260/210 AB

[56] References Cited
UNITED STATES PATENTS

| | | | |
|---|---|---|---|
| 3,832,286 | 8/1974 | Weinstein et al. | 260/210 AB |
| 3,868,360 | 2/1975 | Daniels et al. | 260/210 AB |
| 3,880,828 | 4/1975 | Mallams et al. | 260/210 AB |

*Primary Examiner*—Johnnie R. Brown
*Attorney, Agent, or Firm*—Carver C. Joyner; Raymond A. McDonald; Stephen B. Coan

[57] ABSTRACT

A novel composition having antibiotic activity is produced by fermentation of the new species of microorganism, *Micromonospora grisea*. The antibiotic complex is composed of four components, Verdamicin I, sisomicin, Antibiotic G-418, and gentamicin A, of which Verdamicin I is a novel basic antibiotic possessing a broad antibacterial spectrum. The other components have been produced previously.

7 Claims, 2 Drawing Figures

INVENTORS:
MARVIN J. WEINSTEIN
GERALD H. WAGMAN
BY JOSEPH A. MARQUEZ

STEPHEN B. COAN
CARVER C. JOYNER
AGENTS

ANTIBIOTICS SISOMICIN AND VERDAMICIN I AND COMPLEX CONTAINING SAME

This application is a continuation-in-part of our copending Application Ser. No. 426,163 filed Dec. 19, 1973 (now abandoned) which in turn is a continuation-in-part of application Ser. No. 208,907 filed Dec. 16, 1971 (now abandoned) which in turn is a continuation-in-part of our copending application Ser. No. 58,050, filed July 24, 1970 (now abandoned).

This invention relates to novel complex having antibiotic activity and to a fermentation process for the production thereof.

The fermentation process aspect of this invention comprises cultivating a microorganism of the species *Micromonospora grisea*, a hitherto unknown species of the genus *Micromonospora* under aerobic conditions in an aqueous nutrient medium containing assimilable sources of carbon and nitrogen until a composition of matter having substantial antibiotic activity is obtained and recovering said composition from said medium.

The invention also relates to novel antibiotic substances and to non-toxic derivatives thereof such as acid addition salts and Schiff base-oxazolidine derivatives.

A further aspect of the present invention pertains to a process for the separation of the plurality of antibiotic components of said complex.

The complex and the individual components thereof exhibit a broad spectrum of antibacterial activity, and therefore, may be used in wash solutions for cleaning laboratory and hospital equipment. They may also be used to treat laboratory animals harboring or infected with susceptible bacteria.

THE MICROORGANISM

The microorganism *Micromonospora grisea* (sometimes referred to herein as *M. grisea*) was obtained from soil sampled in the vicinity of Topeka, Kansas. The microorganism has been deposited with the United States Department of Agriculture, Northern Utilization Research and Development Division, Peoria, Illinois, from whom subcultures are available, and has been assigned the numerical designation NRRL 3800.

It is to be understood that the process of the subject invention, though described in detail with particular reference to the novel microorganism *Micromonospora grisea* NRRL 3800, is not limited to this particular microorganism or to microorganisms fully described by the cultural characteristics disclosed herein. It is intended that this invention also include other strains or mutants of the said microorganism which can be produced by procedures well known in the art, for example, by subjecting the novel microorganism to X-ray or ultraviolet radiation, nitrogen mustard, phage exposure, and the like.

Further, an important characteristic of said microorganism variant or mutant is the ability to product the antibiotic complex described hereinbelow.

*Micromonospora grisea* produces a gray-green pigment when cultivated on various media such as the characterization medium set forth below. The most distinguishing characteristic of *Micromonospora grisea* is its ability under controlled conditions, to elaborate a product which consists of at least 4 components, to be defined hereinafter, together with minor amounts of other substances yet to be identified.

| Characterization Medium | |
|---|---|
| Difco Yeast | 0.5% |
| Sucrose | 3.0% |
| Calcium Carbonate | 0.1% |
| Difco Agar | 1.5% |
| Water (Distilled) | 1.0 liter |

When the sterilized medium is inoculated with *Micromonospora grisea* and incubated at 26°–28° C for 24 days, the following color developments are observed:

Sporulation area: Slate green g. 23*li*, grayish green 150; on prolonged incubation; the sporulation area may turn black.

Vegetative area: Lt. tan g3gc, light yellowish brown 76

The first color designation used herein is according to the Color Harmony Manual (1958), Container Corporation of America. The second designation is from the National Bureau of Standards, Circular 553, November 1, 1955 (U.S.A.) and is the synonym or near synonym of the first designation.

Micromonospora may be further characterized by the taxonomical data given in Table I.

Table I

| Medium: 3% NZ Amine Type A, 1% Dextrose, 1.5% Agar | |
|---|---|
| Organism | Observations |
| | (21 days after inoculation) |
| Macroscopic | Microscopic |
| Growth fair, plicate periphery: (g3gc) Lt. tan, light yellowish brown 76. Center: (g3li) beaver, dark grayish yellowish brown 81. | Mycelium long, sparingly branched 0.5–0.8 $\mu$ in diameter. Spores relatively abundant, produced singly, appearing brown colored by transmitted light, 1.0–1.5 $\mu$ in diameter, appear to be rough walled. |

In addition to the foregoing taxonomical data, the table below sets forth the growth and other characteristics of Micromonospora grisea on a variety of art recognized media:

Table II

| Medium | Growth and Other Characteristics of Micromonospora grisea |
|---|---|
| Czapeks Medium (Glucose) | Growth: Poor, non-descriptive |
| Asparagine-Glucose Medium | Growth: Fair to poor, granular, light brown g3lg, moderate yellowish brown 77 |
| Calcium Malate Agar | Growth: Poor, non-descriptive |
| Ordinary Agar (Water Agar) | Growth: Poor, non-descriptive |
| Nutrient Agar | Growth: Poor, non-descriptive |
| Loeffler's Serum Medium (Difco) | Growth: Poor, no reaction |
| Potato Plug | Growth: Good, plicate, light tan g3gc, light yellowish brown 76 |
| Peptone Glucose Agar | Growth: Poor, non-descriptive |
| Egg Agar (Dorset Egg Medium Difco | Growth: Poor, no reaction |
| Starch Agar | Growth: Good, plicate-furrowed, no aerial mycelium. Color: Mustard Brown g2N1, Moderate Olive 107 |

Table II-continued

| Medium | Growth and Other Characteristics of Micromonospora grisea |
|---|---|
| | Hydrolysis: Positive |
| Litmus Milk (Difco) | Partially peptonized |
| Cellulose Medium | Decomposition very slow, requiring 3 – 6 months or longer. |
| Bennett's Agar | Growth: Good, plicate, g24ml ivy, dark grayish green 151 |
| Emerson's Agar | Growth: Fair, flat, g3gc, light tan, light yellowish brown 76 |
| Tomato Paste Oatmeal Agar | Growth: Fair, raised, furrowed, g4ga apricot, light orange 52 |
| Glucose Yeast Extract Agar | Growth: Good, plicate, g31E, camel-moderate yellowish brown 77 |
| Potato Slice | Growth: Good, plicate, light tan g3gc, light yellowish brown 76 |
| Sucrose Nitrate Agar (Czapek's Agar) | Growth: Fair, flat g3ec - light beige = light grayish yellowish brown 79 |
| Tyrosine Agar | Growth: Poor, no color reaction |
| Observations at 2, 7 and 14 days (after Gordon and Smith J. Bact. 69:147) Peptone Iron Agar Observations at 2, 7 and 14 days | Growth: Fair, no color reaction |
| Glucose Asparagine Agar | Growth: Fair to poor, granular, g3lg, lt. brown, moderate yellowish brown 77 |
| Milk | Hydrolysis: Positive, Growth: Poor |
| Cellulose | Very slowly decomposed |

*Micromonospora grisea* reduces nitrate, grows well on gelatin causing hydrolysis and grows in media containing 1.5% sodium chloride but does not grow in the same media containing 3% sodium chloride.

*Micromonospora grisea* requires assimilable sources of carbon and nitrogen for good growth and antibiotic production. A wide range of such sources may be applied. Table 3 gives some examples of nitrogen sources and indicates qualitatively the growth of the microorganism.

Table III

UTILIZATION OF NITROGEN SOURCES

| Nitrogen Source (+1% Glucose) | Growth Observation |
|---|---|
| 0.5% Difco Yeast Extract | Good |
| 1.0% NZ Amine Type A | Good |
| 1% Asparagine | Poor |
| 1% Glutamic Acid | Poor |
| 1% Sodium Nitrate | Poor |
| 1% Ammonium Nitrate | Poor |

The microorganism exhibits good growth on the following carbohydrates, α-arabinose, 1-arabinose, d-glucose, d-levulose, mannose, d-galactose, sucrose, d-xylose and starch. It exhibits poor growth on dulcitol, glycerol, l-inositol, β-lactose, d-mannitol, melibiose, melizitose, raffinose, 1-rhamnose and salicin. The control medium consists of 0.5% yeast extract in which poor growth is exhibited in the absence of a suitable carbohydrate.

The Fermentation

The fermentation of Micromonospora grisea to produce an antibiotic complex is usually conducted in two or three stages. The first stage or first two stages are devoted to germination of the microorganism to produce a suitable inoculum and is usually effected at a temperature in the range of from about 25° to about 35° C for 1 to 4 days. Further, the germination stage is effected under aerobic conditions with agitation, preferably rotary agitation.

The fermentation (production) stage is commenced by inoculating under sterile conditions a suitable medium with the previously prepared inoculum. The production stage of the fermentation is usually effected at the same temperature range as the germination stage. Further, it usually requires from about 4 to about 7 days to reach peak production. Unlike the germination stage where the pH usually remains fairly stable the production stage requires regulation of the pH to the range of from about 7.2 to about 8.3. When peak antibiotic activity is attained (as determined by an assay to be described hereinbelow), the antibiotic complex is isolated by standard isolation techniques such as the following.

Isolation of the Antibiotic

The antibiotic composition obtained by the fermentation process described above is removed from the fermentation broth by adsorption on a weakly acidic ion exchange resin (e.g. IRC-50), preferably in the ammonium cycle. The procedure is substantial as follows: Oxalic acid, approximately 5 to 8 grams/liter of fermentation is added to the whole broth to precipitate calcium as the insoluble oxalate salt and the pH of the fermentation adjusted to 2.0 with strong mineral acid, e.g. 6N sulfuric acid to release the antibiotic from the mycelium. After filtration, the clarified broth is neutralized with ammonium hydroxide, the antibiotics adsorbed on Amberlite IRC-50 $NH_4^+$ 20–50 mesh (Rohm and Haas, Philadelphia, Pennsylvania) ion exchange resin and the spent (extracted) broth discarded. The antibiotic composition is eluted from the resin with base, preferably 2N ammonium hydroxide, the eluate concentrated to a small volume in vacuo and ultimately evaporated to dryness.

SEPARATION OF THE FOUR MAJOR ACTIVE COMPONENTS OF THE ANTIBIOTIC PRODUCT

Detection of the antibiotic and determination of homogeniety of fractions is carried out by paper chromatography and is accomplished by two methods: 1) by the use of reagents, and 2) by a microbial procedure. The first method is carried out by spraying the paper chromatograms with 0.25% ninhydrin in pyridine-acetone and subsequent heating at 105° C for several minutes. The zones appear as colored spots against a white background.

Microbial detection of the antibiotic zone is carried out by laying the paper on an agar plate seeded with *Staphylococcus aureus* ATCC 6538P. After 10 minutes the paper is removed and after a suitable incubation period (usually 16–18 hours) the zones of inhibition representing the antibiotics are observed. These and similar tests show that the antibiotic product obtained by the fermentation process described above consists of a plurality of components. Four of the components appear to constitute the major part of the product.

The separation is achieved by a number of art recognized techniques such as, counter-current extraction, chromatography on ion exchange resins, chromatography on other solid adsorbents such as silica gel, chromsorb, cellulose and the like. We prefer silica gel chromatography. The four components are eluted with the lower phase of a solvent mixture consisting of chloroform, isopropanol, and concentrated ammonium hydroxide (2:1:1 v/v) until the first two components are removed and elution continued with the lower phase of a 1:1:1 mixture of the same solvents until desorption of the remaining antibiotics is complete.

The antibiotics are named in accordance with their mobility down the column. Thus, the first to be eluted is Verdamicin I, the second is Verdamicin II, etc. In addition to the major components, it is sometimes possible to detect the presence of other antibacterial materials. However, these materials are produced in such minute quantities that isolation, purification and characterization of the same has not been successfully accomplished. For example, a crude extract containing substantially all the antibiotics produced in the fermentation was reduced in volume to form a syrupy concentrate. The concentrate was then subjected to ascending chromatography on Chromar 500 for about 1 hour using a system consisting of chloroform, methanol and concentrated ammonium hydroxide (1:1:1 v/v). When the chromatogram was bioautographed against Staphylococcus aureus ATCC 6538P, small quantities of three additional fermentation products were barely detectable. These products had the following $R_f$ values (as nearly as could be determined) 0.41, 0.30 and 0.12 whereas the major components had the $R_f$ values shown in Table 5 below.

The biological properties of sisomicin are described in the Journal of Antibiotics Vol. XXIII No. 11, pages 551–565. The preparation and properties of the antibiotic are disclosed in Belgian Patent No. 735,145.

The antibacterial properties of gentamicin A are set forth by Weinstein et al in Antimicrobial Agents and Chemotherapy 1965, pages 816–820 and its structure was published by Machr and Schaffner in the Journal of the American Chemical Society 89:25, December 6, 1967.

The biological and physico-chemical properties of Antibiotic G-418 are set forth in co-pending application Ser. No. 196,707, filed Nov. 8, 1971, which is of common ownership with this application. Comparison of the biological and physico-chemical properties of Antibiotic G-418 with those of Verdamicin III, conclusively establish that the two compounds are identical.

Physico-chemical analyses of Verdamicin II and Verdamicin IV, and on derivatives of these compounds conclusively establish that they are in fact the previously known antibiotics, sisomicin and gentamicin A, respectively.

Physico-chemical analyses on Verdamicin I indicates that it is a novel substance but one which is structurally similar to gentamicin $C_2$. Hydrolysis of the two antibiotics with 6N hydrochloric acid at 100° C for 2 hours followed by paper chromatography on either a solvent system consisting of (1) n-butanol:pyridine:water:acetic acid in the ratio of (6:4:3:1 v/v) or (2) propanol:-pyridine:water:acetic acid in the ratio of (6:4:3:1 v/v), and spraying the chromatograms with ninhydrin, clearly reveals that gentamicin $C_2$ and Verdamicin I give hydrolysis products that differ. In both systems the hydrolysates indicate the presence of two common Table V Comparative $R_f$ and $R_t$ Values

| Paper Chromatographic Systems | $R_t$'s of Antibiotics | | | | Gentamicin Components | | |
|---|---|---|---|---|---|---|---|
| | Verdamicin | | | Sisomicin | | | |
| | I[a] | II[b] | III[c] | (Sch 13475) | $C_1$ | $C_2$ | $C_{1a}$ |
| Chloroform:methanol: conc. ammonium hydroxide (1:1:1) on Chromar 500 sheet, ascending | 0.65 | 0.58 | 0.41 | 0.58 | 0.74 | 0.65 | 0.57 |
| | $R_t$'s of Antibiotics, t = 6 hours[e] | | | | | | |
| Chloroform:methanol: 17% ammonium hydroxide 2:1:1 on Whatman No. 1 paper, descending | 0.40 | 0.21 | 0.05 | 0.21 | 0.67 | 0.40 | 0.21 |
| | $R_t$'s of Antibiotics, t = 16 hours | | | | | | |
| 2 butanone:tert-butanol:methanol: conc. ammonium hydroxide 16:3:1:6 on Whatman No. 1 paper, descending | 0.44 | 0.36 | 0.27 | 0.34 | 0.57 | 0.47 | 0.38 |

[a]verdamicin I component
[b]verdamicin II component (sisomicin)
[c]verdamicin III component (Antibiotic G-418)
[d]verdamicin IV (gentamicin A)

[e]$R_t = \frac{\text{distance of zone from origin}}{\text{distance from origin to end of paper}}$ at time t

The Antibiotic

The $R_T$ and $R_f$ values set forth above indicate that Verdamicin II, Verdamicin III and Verdamicin IV are chromatographically indistinguishable from sisomicin (Antibiotic 6640), Antibiotic G-418 and gentamicin A, respectively.

products one of which is 2-deoxystreptamine. The remaining hydrolysis product from Verdamicin I, however, is unlike the corresponding one from gentamicin $C_2$.

Based upon the physical and chemical data set forth below and upon analysis of its hydrolysis products, Verdamicin I is believed to have the following structural gross formula without stereochemical assignments.

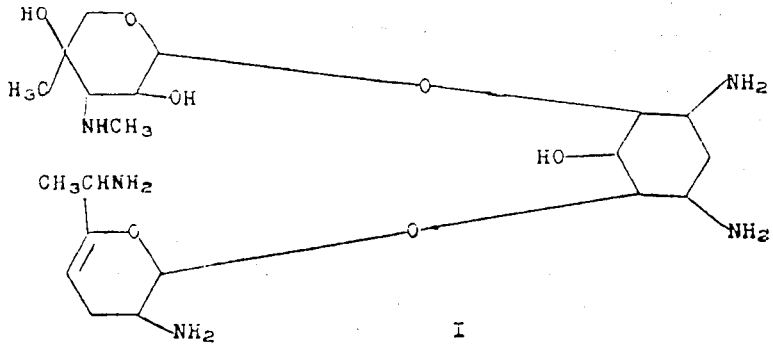

I

Verdamicin I may also be depicted stereochemically as shown in formula 1a.

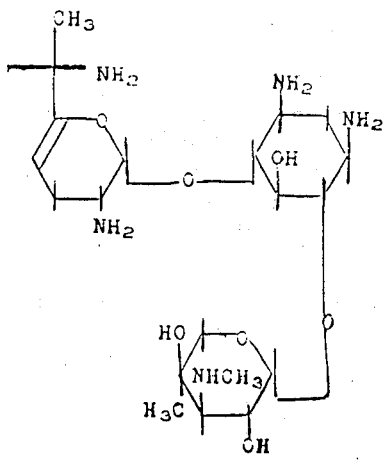

1a

Verdamicin I being a basic compound readily forms non-toxic acid addition salts with organic and inorganic acids. Exemplary of such acids are sulfuric, hydrochloric, phosphoric, toluenesulfonic, succinic, maleic, acetic, propionic, cyclopropane carboxylic, adamantane carboxylic, furoic, benzoic and phenylacetic acids and the like. The compounds contemplated also include the alkali metal derivatives of the antibiotic salts of dibasic or tribasic acids. In general, these salts are water soluble and may be formed by treatment of an aqueous solution of the antibiotic with a stoichiometric amount of acid and lyophilizing the resulting solution. Optionally, the salts may be precipitated from an aqueous solution by the addition of miscible organic solvents such as lower alkyl ketones (e.g. acetone) lower alcohols (e.g. methanol), cyclic ethers (e.g. tetrahydrofuran), or lower tertiary amides such as dimethylformamide, diethylacetamide and the like. Verdamicin I readily forms solvates and hydrates from which it is difficult to obtain the unsolvated or the anhydrous antibiotic. Consequently, the elemental analysis set forth in Table 6 below is in excellent agreement with the antibiotic as the trihydrate (i.e. $C_{20}H_{39}O_7N_5 \cdot 3H_2O$). The non-toxic acid addition salts of Verdamicin I are also broad spectrum antibacterial agents having substantial potency against most of the more prevalent species of infectious organisms.

Verdamicin I also forms antibacterial Schiff base-oxazolidine derivatives with aldehydes by procedures that are known in the art. The Schiff base-oxazolidine derivatives contemplated herein are those formed by condensing verdamicin with aldehydes having up to about 12 carbon atoms and being selected from the group consisting of aliphatic, alicyclic, aromatic and heterocyclic, compounds. Exemplary of the foregoing are such aldehydes as acetaldehyde, furfural, cyclopentylacetaldehyde, pyridoxal, veratraldehyde, butraldehyde acrolein, salicyaldehyde, succinaldehyde, crotonaldehyde, benzaldehyde and the like.

These Schiff base-oxazolidine derivatives of verdamicin may be employed as a solution in organic solvents (e.g. as a tincture). They may also be employed in topical creams and ointments where compatibility with lipoid substances is beneficial.

In table VI below are set forth physical properties of Verdamicin I as the hydrated free nitrogen base and as the sulfuric acid addition salt (sulfate).

Table VI

Chemical and Physical Properties of Verdamicin I

| Elemental Analysis | Base[1] Average of 2 | Average of 2 | Sulfate Average of 2 | Average of 2 |
|---|---|---|---|---|
| C | 47.98 | 48.04 | 31.10 | 30.95 |
| H | 8.13 | 8.22 | 6.61 | 6.60 |
| N | 13.43 | 13.28 | 8.99 | 8.69 |
| O (by diff.) | 30.45 | 30.47 | | |
| $SO_4$ | — | — | 29.30 | — |
| Rotation (water) | +155.7 c=0.3% | +167.1 c=0.3% | +96.5 c=0.3% | +99.4 c=0.3% |
| Equivalent weight | 108.5 | 104.9 | | |
| pKa | 8.1 | 8.1 | | |
| Empirical formula $C_{20}H_{39}O_7N_5$ | | | | |

[1] Analyses consistent with $C_{20}H_{39}O_7N_5 \cdot 3H_2O$

Verdamicin I exhibits no absorption in the ultraviolet range of 220–400 m$\mu$. Further, it is stable to boiling for at least thirty (30) minutes in 0.1 molar buffers in the pH range of 2 – 10.

Verdamicin I sulfate has a characteristic infrared absorption spectrum in mineral oil (Nujol) as shown in FIG. 1. The more characteristic absorption bands are set forth in table VII below.

Figure 2:
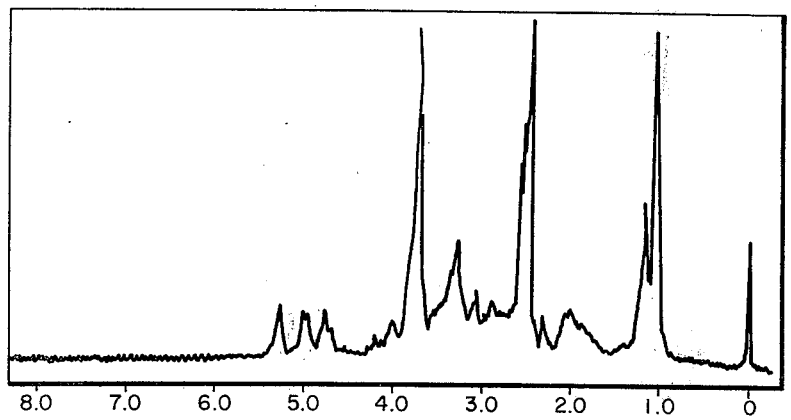

Verdamicin I (free base) has a characteristic nuclear magnetic resonance (NMR) spectrum as shown by FIG. 2. The NMR spectrum was obtained by the use of a Varian A-60-A spectrometer (Varian Associates, 611 Hansen Way, Palo Alto, California) on a solution of about 0.31 ml. containing about 22 mg. of antibiotic in a deuterium oxide ($D_2O$)-dimethyl sulfoxide (DMSO) mixture. The spectrum is recorded in parts per million (PPM) from 3-(trimethylsilyl)-propanesulfonic acid sodium salt, the internal standard.

Table VII

Characteristic Infrared Absorption Bands
Verdamicin I Sulfate

| | | | | | |
|---|---|---|---|---|---|
| 2.9 – 3.8 | μ | (VS, V brd.) | 7.25 | μ | (Nujol) |
| 3.38 – 3.52 | μ | (Nujol) | 7.75 | μ | (W–M) |
| 4.25 | μ | (Shd.) | 8.6 – 9.6 | μ | (VS, V brd.) |
| 4.80 | μ | (W, brd.) | 10.30 | μ | (W – M) |
| 5.93 | μ | (Shd.) | 10.92 | μ | (Shd.) |
| 6.16 | μ | (MS) | 11.42 | μ | (W) |
| 6.50 | μ | (MS) | 12.10 | μ | (VW, brd.) |
| 6.83 | μ | (Nujol) | 12.75 | μ | (VW, brd.) |

Notations:
brd. = broad;
M = medium;
Shd. = shoulder;
S = strong;
V = very;
W = weak Biological Assay Th microbiological assay of the antibiotic substances is a disc plate assay using *Staphylococcus aureus* ATCC 6538P as test organism. The physical conditions of the assay are similar to those described for gentamicin (Oden et al, Antimicrobial Agents and Chemotherapy - 1963, American Society for Microbiology). The standard Verdamicin I base has a defined potency of 1000 meg/mg. One meg. of standard under the conditions of this assay will produce a zone of inhibition of $17.0 \pm 1.3$ mm.

Verdamicin I base assays 1000 meg/mg in the gentamicin assay and, significantly, the dose response curve of verdamicin is parallel to that of gentamicin. Verdamicin I sulfate assays 674 meg/mg in the gentamicin assay and 695 meg/mg against its own base as the comparison standard.

Biological Activity of the Mixture

The antibiotic composition obtained above exhibits a broad spectrum of antibacterial activity when tested in vitro against gram-positive and gram-negative bacteria. The table below shows the minimum inhibitory concentrations of the antibiotic mixture against representative species of bacteria and yeast. The tests were performed in yeast beef broth (pH 7.4).

| Organism | MIC (mcg/ml) |
|---|---|
| Bacillus subtilis 6633 | 0.03 |
| Staphylococcus aureus 209P | 0.8 |
| Staphylococcus aureus G | 0.3 |
| Streptococcus pyogenes C | 3.0 |
| Escherichia coli 10536 | 0.8 |
| Escherichia coli 3 | 0.8 |
| Klebsiella sp. 803 | 0.8 |
| Proteus sp. 126 | 0.8 |
| Proteus sp. Mc Fadden | 0.3 |
| Pseudomonas aeruginosa Sc | 0.3 |
| Pseudomonas aeruginosa 13 | 0.3 |
| Salmonella sp. Sc. | 3.0 |

Biological Activity of Verdamicin I

In Vitro

Verdamicin I exhibits a broad spectrum of antibacterial activity when tested in vitro against representative gram positive and gram-negative bacteria. It is active against kanamycin resistant bacteria but appears to be cross resistant with gentamicin. The antibiotic does not exhibit any substantial in vitro activity against yeast.

In table VIII are set forth the minimum inhibitory concentrations of Verdamicin I sulfate against representative species of bacteria and yeast. The tests were performed in yeast beef broth (pH 7.4), inhibition being determined after 24 hours and again after 48 hours. Results obtained with gentamicin sulfate are also set forth for comparison.

Table VIII

Minimum Inhibitory Concentration — MIC (mcg/ml)
Verdamicin I Sulfate

| Organism | 24 hours | 48 hours | Gentamicin Sulfate 24 hours |
|---|---|---|---|
| Staphylococcus aureus 209P | 0.3 | 0.75 | 0.1 |
| Streptococcus pyogenes C | 0.75 | 3.0 | 3.0 |
| Streptococcus pyogenes 6 | 0.3 | 0.75 | 1.0 |
| Aerobacter aerogenes 3 | 0.3 | 0.3 | 0.6 |
| Aerobacter aerogenes 4 | 0.3 | 0.3 | 0.3 |
| Escherichia coli Sc | 0.3 | 0.75 | 0.75 |
| Escherichia coli 5 | 0.3 | 0.75 | 0.3 |
| Escherichia coli 19 | 0.3 | 0.3 | 0.3 |
| Klebsiella pneumoniae Ad KR* | 0.3 | 0.3 | 0.3 |
| Klebsiella pneumoniae 17 KR | 0.3 | 0.3 | 0.3 |
| Proteus mirabilis MeF | 0.3 | 0.3 | 0.3 |
| Proteus vulgaris 2 | 0.3 | 0.3 | 0.3 |
| Pseudomonas aeruginosa 8689 | 0.075 | 0.3 | 0.3 |
| Pseudomonas aeruginosa Miller | 0.75 | 0.75 | 0.5 |
| Salmonella paratyphi B1 | 0.3 | 0.75 | 1.0 |
| Salmonella paratyphi B2 | 0.3 | 0.3 | 0.5 |
| Candida albicans 406 | >10 | >10 | >50 |
| Candida albicans 401 | >10 | >10 | >50 |
| Candida albicans 411 | >10 | >10 | >50 |
| Saccharomyces cerevisiae | >10 | >10 | >50 |

*KR — Kanamycin-resistant

In vivo

Verdamicin I was tested against four (4) species of infectious bacteria in mice and was administered as a single subcutaneous dose one (1) hour after infection via intraperitoneal injection of a lethal quantity of pathogen.

In table IX are set forth the results of in vivo tests which show Verdamicin I to be a potent antibacterial agent against both gram-positive and gram-negative organisms. Results obtained with gentamicin are set for comparison. Table IX also sets forth the acute toxicity of Verdamicin I via intraveneous administration.

Table IX

| Organism | Protective Activity in Mice $PD_{50}$ (mg/kg) | | |
|---|---|---|---|
| | Route | Verdamicin I | Gentamicin |
| Staphylococcus aureus Gray | S.C. | 2.5 | 2.4 |
| Streptococcus pyogenes C | S.C. | 1.0 | 5.0 |
| Escherichia coli 10536 | S.C. | 1.5 | 1.7 |
| Pseudomonas aeruginosa 8689 | S.C. | 2.0 | 1.7 |
| Acute Toxicity in Mice | | | |
| | Route | $LD_{50}$ (mg/kg) | |
| | I.V. | 75 | |

Example 1

1. Shake Flask antibiotic production by M. grisea a. Inoculum preparation: Inoculate a 300 ml. flask containing 100 ml. of the following sterile medium with a loopful of M. grisea from an agar slant:

| | | |
|---|---|---|
| Medium A. | Beef extract | 3 gm. |
| | Tryptose | 5 gm. |
| | Yeast extract | 5 gm. |
| | Dextrose | 1 gm. |
| | Starch | 24 gm. |
| | Calcium carbonate | 2 gm. |
| | Tap water | 1000 ml. |

Incubate the flask with continuous agitation on a rotary shaker at 250 to 300 rpm at 25° to 35° C until substantial growth is attained. This usually takes from 1 to about 4 days.

b. Fermentation: Inoculate a 2.0 liter flask containing 500 ml. of either of the two media set forth below with a 5% inoculum prepared in step a:

| | | |
|---|---|---|
| Medium B. | Soybean meal | 30 gm. |
| | Dextrin | 50 gm. |
| | Dextrose | 5 gm. |
| | Calcium carbonate | 7 gm. |
| | Tap water | 1000 ml. |

Ferment the inoculated medium at from about 26° C to about 35° C for from about 4 to about 7 days with continuous agitation on a rotary shaker at 200–300 rpm. Assay the fermentation periodically after the first 48 hours to determine when peak antibiotic production is attained. When peak product is reached, work up the fermentation by the procedure of Example 1.

EXAMPLE 2

14 Liter Tank Fermentation of M. Grisea a. Germination Stage: Transfer a 25 ml. portion of inoculum, prepared as described in Example 1, to a two liter erlenmeyer flask containing 500 ml. of sterile inoculum medium. Incubate the inoculum for from about 2 to about 4 days with continuous agitation at about 280 rpm at about 28° C.

b. Fermentation Stage: Transfer the entire contents of the germination flask to a 14-liter fermentor containing 10 liters of sterile Medium B. Incubate the fermentation mixture at about 35° C with continuous agitation at about 250 – 500 rpm for about 90 hours. Maintain the pH between 7.2 and 8.3 throughout the fermentation while aerating the culture medium with about 3 to about 5 liters of air per minute. Assay the fermentation mixture periodically after the first 48 hours to determine when peak antibiotic activity is attained. When peak production is attained work up the fermentation by the procedure of Example 4.

Example 3

25 gal. Tank Fermentation of M. Grisea

| | |
|---|---|
| Inoculum Stage | |
| Medium C | |
| Yeast extract | 5.0 gm. |
| Beef extract | 3.0 gm. |
| Tryptone | 5.0 gm. |
| Potato Starch | 24.0 gm. |
| Cerelose | 1.0 gm. |
| Calcium carbonate | 1.0 gm. |
| Water | 1.0 liter |

Prepare 1.0 liter of Medium C in the proportions shown above. Adjust the pH to 7.3 and dispense 0.5 liter aliquots in 2 liter Erlenmeyer flasks. Sterilize the medium for 45 minutes at 121° C. Cool to room temperature and inoculate each flask with 5 ml. of a culture of M. grisea. Incubate each flask for 72 hours on a rotary shaker (200 rpm) at 30° C. Transfer the inoculum (25 ml/flask) to 0.5 liters of sterile Medium C and incubate each flask for 48 hours on the rotary shaker at 30° C. Pool 5.0 liters of this inoculum and charge to 90 liters of sterile Medium C, adjust the temperature to 30° C, the pH to about 7.3 – 7.7, the aeration to about 1 – 2 cubic feet per minute, and the agitation to about 200–400 rpm. Continue the fermentation for from about 100 to about 130 hours until peak antibiotic production is attained. Work up to the fermentation by the procedure of Example 4.

EXAMPLE 4

Isolation of the Antibiotic Complex

To 60 liters of fermentation broth obtained by a process as described in Examples 2 or 3, add about 400 grams of oxalic acid with vigorous agitation. Adjust the pH of the fermentation mixture to pH 2.0 with 6N sulfuric acid and agitate for about 20 minutes. Filter the acidified fermentation mixture and retain the filtrate. Wash the mycelial cake with tap water and combine the washings with the filtered broth. At this juncture it is advantageous to combine the filtrates and washings derived from about three 60 liter fermentations (i.e. about 180 liters). Neutralize the combined filtrates and washes with 6N ammonium hydroxide (requires from about 500 to about 900 ml.). Adsorbe the antibiotic complex on IRC-50 in the ammonium form by passing the neutral broth through a column of resin which is 2 inches in diameter and 26 inches high. Adjust the flow rate to about 175–200 ml./minute until all of the broth has been processed. Wash the column color free with deionized water (about 20 liters). Desorb the antibiotic complex with 2N ammonium hydroxide at a rate of about 80 ml/minute followed by deionized water when the effluent pH reaches 10. Concentrate the effluent in vacuo to about 1 liter and lyophilize to obtain the antibiotic complex.

Alternatively, where the effluent is highly colored, a treatment with IRA-401S may be effected. This treatment is usually performed by passing the effluent from the preceding column through a column of IRA-401S (1 dia × 20 inches $h$) at a rate of about 120 ml./minute. Wash the (IRA-401S) column free of antibiotic and concentrate the effluent and washes as described above.

EXAMPLE 5

A. Preparation of the sulfate salt of the Antibiotic Complex

Dissolve 37 g. of the crude complex base obtained according to Example 4 in 1000 ml. water and adjust to pH 4.5 with sulfuric acid. Stir the solution with Darco G60 for about ½ hour and filter. Concentrate the filtrate to about 100 ml. and add to an excess of methanol. Filter off the resulting precipitate of the mixed sulfates and dry under vacuum.

B. Transformation of the sulfate salt into the Antibiotic Complex base

Suspend the mixed sulfates obtained according to step A in 1000 ml. of chloroform and bubble ammonia gas through the suspension for about one-half hour. Filter the mixture and evaporate the filtrate to dryness to obtain the Antibiotic complex base.

EXAMPLE 6

Isolation of Verdamicin I, Sisomicin, Antibiotic G-418, and Gentamicin A

Suspend 12 lbs. of silica gel in the lower phase of a solvent mixture composed of isopropanol: chloroform: concentrated ammonium hydroxide (1:2:1 v/v). Transfer the suspension into a chromatographic column having an inner diameter of about 4 inches.

Suspend 100 g. of antibiotic complex as obtained from Example 4 in about 1.0 liter of the lower phase of the solvent system used to prepare the chromatographic column. Filter the so obtained suspension and retain the insolubles for further processing. Concentrate the filtrate to approximately 1.0 liter prior to placing atop the column.

With heating and stirring, dissolve the previously obtained insoluble material (approximately 66g.) in methanol and filter to remove the inorganic material present (about 6 g.). Cool the methanolic solution with exposure to air and refilter to remove most of the sparingly soluble gentamicin A carbonate.

Adsorb the antibiotic complex, from which most of the gentamicin A has been removed, on the silica gel column prepared above and develop the chromatogram with the solvent mixture taking 2.0 liter fractions with the column at full flow. When the Verdamicin II is desorbed (which normally takes from about 90 to about 100 fractions), the ratio of solvents is changed to 1:1:1 and elution continued until the remaining material is desorbed. Generally, in effecting the separation of the antibiotic complex on a column of this size, the number of fractions collected is from about 250 to about 350. Spot each fraction on filter paper and test with ninhydrin reagent to determine the presence or absence of antibiotic, i.e. ninhydrin positive material. Subject those fractions containing antibiotic substances to paper chromatography in a system consisting of chloroform:methanol:17% ammonium hydroxide (2:1:1 v/v) followed by bioautography against *Staphylococcus aureus* ATCC 6538P, to determine which fractions contain the same antibiotic. Combine the fractions in accordance with the determination made by chromatography and bioautography, concentrate the combined fractions in vacuo to about 100 ml. and lyophilize.

The distribution of antibiotics from the column is substantially as follows:

| Fractions | Antibiotics |
|---|---|
| 1 – 65 | Inactive organic materials |
| 66 – 87 | Verdamicin I |
| 88 – 91 | Sisomicin |
| 119 – 259 | Antibiotic G-418 |
| 259 – end | Residual gentamicin A |

EXAMPLE 7

Preparation of Verdamicin I Sulfate

Dissolve 500 mg. of Verdamicin I prepared according to the process of Example 6, in 90 ml. of water and adjust the pH of the solution to 4.5 with dilute sulfuric acid. Stir the solution with 1 to 2 g. of decolorizing charcoal (Darco G-60) for about 30 minutes and filter. Concentrate the filtrate in vacuo to about 10 ml. and pour into about 100 ml. of methanol with stirring. Filter the resulting suspension, wash with fresh methanol and dry obtaining thereby about 450 mg. of Verdamicin I sulfate.

EXAMPLE 8

Preparation of Verdamicin I Hydrochloride

Dissolve 400 mg. of Verdamicin I as prepared in Example 6 in about 75 ml. of water and adjust the pH of the solution to 4.5 with dilute hydrochloric acid. Stir the solution with 1 to 2 g. of decolorizing charcoal (Darco G-60) for about 30 minutes and filter. Concentrate the filtrate in vacuo to about 75 ml. and pour into 150 ml. of a methanol:acetone (1:2 v/v) mixture with stirring. Filter the resulting suspension, wash with fresh acetone and dry obtaining thereby about 300 mg. of Verdamicin I hydrochloride.

The foregoing procedure is of general applicability and may be used with an equivalent quantity of other acids such as phosphoric, acetic, propionic, cyclopropane, carboxylic, adamantane carboxylic, furoic, benzoic, phenylacetic, toluenesulfonic, succinic and maleic acids to form nontoxic acid addition salts which are the functional equivalent of Verdamicin I hydrochloride and of Verdamicin I sulfate.

EXAMPLE 9

Preparation of Verdamicin I Base

Dissolve 390 mg. of Verdamicin I sulfate, as prepared in Example 7, in 10 ml. of water. Prepare an IRA-401S column (Amberlite anion exchange resin, Rohm and Haas) having the following dimensions: height, 25 cm; outside diameter, 2 cm. Charge the antibiotic solution to the resin column and elute with deionized water until the eluate is negative to ninhydrin reagent. Concentrate the eluate to about 25 ml. and lyophilize obtaining thereby 230 mg. of Verdamicin I.

We claim:

1. A complex having antibiotic activity, said complex consisting essentially of Verdamicin I, sisomicin, Antibiotic G-418, and gentamicin A.

2. A complex having antibiotic activity, said composition consisting essentially of non-toxic acid addition salts of Verdamicin I, sisomicin, Antibiotic G-418 and gentamicin A.

3. A compound selected from the group consisting of Verdamicin I having the formula:

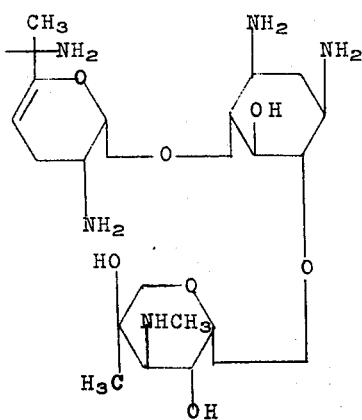

and the non-toxic acid addition salts and the Schiff base-oxazoladine derivatives thereof, said derivatives being derived from aldehydes having from 1 to 12 carbon atoms.

4. A compound according to claim 3, said compound being Verdamicin I.

5. A compound according to claim 3, said compound being a non-toxic acid addition salt of Verdamicin I.

6. A compound according to claim 5, said compound being Verdamicin I hydrochloride.

7. A compound according to claim 5, said compound being Verdamicin I sulfate.

* * * * *